US00PP18931P2

(12) United States Plant Patent
Scott et al.

(10) Patent No.: US PP18,931 P2
(45) Date of Patent: Jun. 17, 2008

(54) ***CORDYLINE* PLANT NAMED 'FALCON'**

(50) Latin Name: *Cordyline baueri*
Varietal Denomination: Falcon

(76) Inventors: Gordon Scott, 9A Kowhai Road, Whenuapai (NZ); Sally Scott, 9A Kowhai Road, Whenuapai (NZ)

( * ) Notice: Subject to any disclaimer, the term of this patent is extended or adjusted under 35 U.S.C. 154(b) by 307 days.

(21) Appl. No.: 11/254,488

(22) Filed: Oct. 20, 2005

(51) Int. Cl.
*A01H 5/00* (2006.01)

(52) U.S. Cl. ..... Plt./383
(58) Field of Classification Search ..... Plt./383
See application file for complete search history.

(56) References Cited

PUBLICATIONS

GTITM UPOVROM Citation for 'Falcon' as per NZ PBR TRM 069; Aug. 22, 2003.*

* cited by examiner

*Primary Examiner*—Kent Bell

(57) ABSTRACT

A new cultivar of *Cordyline* plant named 'Falcon' that is characterized by red-brown leaves and a compact habit.

1 Drawing Sheet

Botanical classification: *Cordyline baueri*. Variety denomination: 'Falcon'.

BACKGROUND OF THE INVENTION

The present invention relates to a new and distinct cultivar of *Cordyline baueri* and hereinafter referred to by the cultivar name 'Falcon'. The new cultivar was discovered by the inventor in a seed bed of *Cordyline baueri* in a cultivated area of Whenuapai, New Zealand in 1999. The exact parents are unknown. 'Falcon' was selected as a single plant.

The new *Cordyline* plant 'Falcon' is distinct and unique due to its red-brown leaves and compact habit.

The new cultivar was first asexually propagated by tissue culture in Hastings, New Zealand in 2000. Since that time, under careful observation, the unique characteristics of the new cultivar have been uniform, stable and reproduced true to type in successive generations of asexual reproduction.

SUMMARY OF THE INVENTION

The new *Cordyline* 'Falcon' is distinguished from other known varieties of *Cordyline,* by the following characteristics:

1. Compact habit.
2. Red-brown leaves.

The closest comparison cultivars are *Cordyline* 'Purple Towel' (not patented) and *Cordyline* 'Red Star' (not patented). 'Falcon' is distinguishable from 'Purple Towel' by its compact habit and deep root system. 'Falcon' is distinguishable from 'Red Star' by its compact habit and red-brown leaf color.

BRIEF DESCRIPTION OF THE DRAWINGS

The accompanying color photograph illustrates the distinguishing characteristics of the new cultivar 'Falcon'. The photograph shows an overall view of a 2 year old plant. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Cordyline* cultivar named 'Falcon'. Data was collected in Whenuapai, New Zealand from 2.5 year old plants. The plants were grown outdoors under natural conditions. The time of year was Winter (Southern Hemisphere). Phenotypic differences may be observed with variations in environmental, climatic, and cultural conditions, without however, any difference in genotype. Color determinations are in accordance with the 1995 Royal Horticultural Society Color Chart except where general color terms of ordinary dictionary significance are used. The growing requirements are similar to the species and no disease problems have been observed.

Botanical classification: *Cordyline baueri* 'Falcon'.
Common name: Cabbage Tree.
Parentage: The parents of 'Falcon' are unknown.
Type: Ornamental perennial.
Growth rate: 5 cm. per month.
Habit: Upright, clump forming.
Height: 70 cm. in height.
Spread: 80 cm. in width.
Hardiness: USDA zone 6 to zone 10.
Propagation method: Tissue Culture.
Vigor: Medium.
Root system: Fine and fibrous.
Pinching: No.
Stem:
- *Number of stems.*—1.
- *Shape.*—Round.
- *Surface.*—Smooth.
- *Color.*—183A.
- *Size.*—Average 3 cm. in diameter, 50 cm. in length.
- *Internode length.*—1 mm.
- *Strength.*—Strong.

Foliage:
- *Leaf dimensions.*—Average 40 cm. in length and 7 cm. in width.
- *Leaf shape.*—Lanceolate.
- *Leaf division.*—Simple.
- *Apex.*—Acute.

*Base.*—Attenuate.
*Margins.*—Entire.
*Color of mature leaves* (*upper and lower surfaces*).—200B with patches of 152B.
*Color of young leaves* (*upper and lower surfaces*).—200B.
*Upper and lower surfaces.*—Smooth.
*Petiole color.*—200B.
*Length.*—1 cm. in length.
*Width.*—2 mm. in width.

Flowers:
*Inflorescence arrangement.*—Terminal panicles.
*Inflorescence size.*—31 cm. in length and 22 cm. in width.
*Quantity of flowers.*—Approximately 800.
*Bud shape.*—Ovate.
*Bud color.*—198C.
*Flower shape.*—Star shaped.
*Flower size.*—3 cm. in diameter.
*Number of petals.*—6.
*Petal color.*—158D.

Disease and pest resistance: Has not been observed.

It is claimed:

1. A new and distinct variety of *Cordyline* plant named 'Falcon' as described and illustrated.

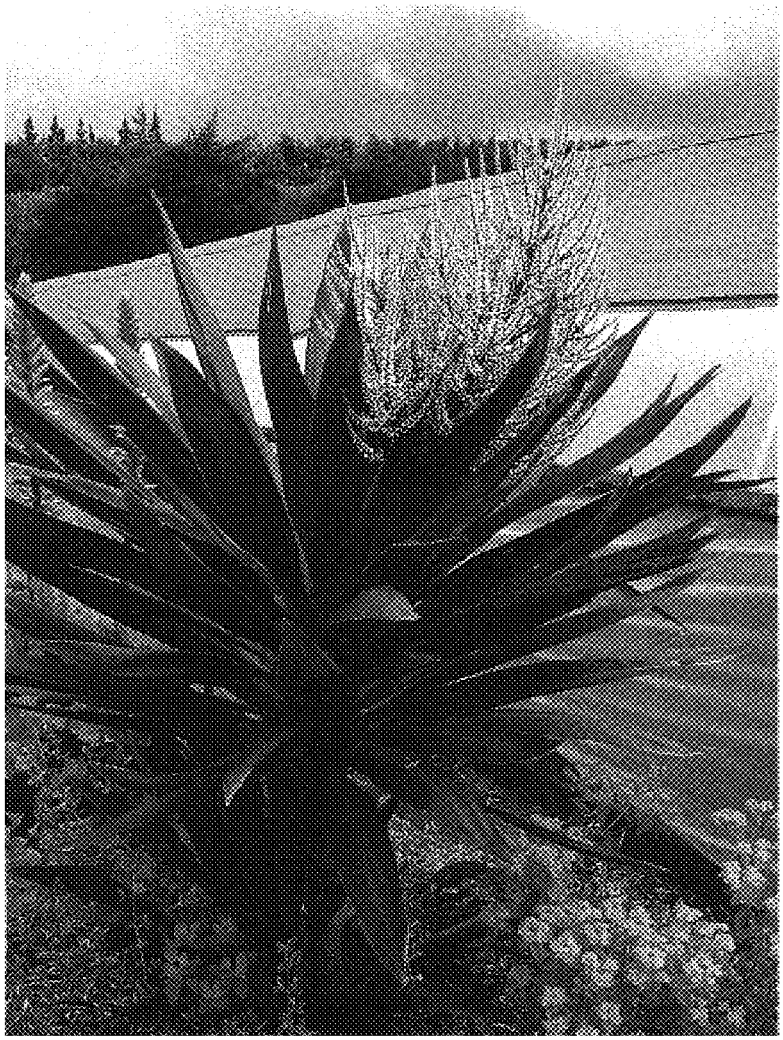

* * * * *